United States Patent [19]

Benziger

[11] 4,032,377

[45] June 28, 1977

[54] METHOD FOR THE PRODUCTION OF HIGH-PURITY TRIAMINOTRINITROBENZENE

[75] Inventor: Theodore M. Benziger, Santa Fe, N. Mex.

[73] Assignee: The United States of America as represented by the United States Energy Research and Development Administration, Washington, D.C.

[22] Filed: July 19, 1976

[21] Appl. No.: 706,403

[52] U.S. Cl. .............................. 149/105; 260/645
[51] Int. Cl.$^2$ .................. C06B 25/04; C07C 79/10
[58] Field of Search ............ 149/105, 106, 107, 99, 149/103; 260/645, 646, 644

[56] References Cited

UNITED STATES PATENTS

| 3,185,738 | 5/1965 | Cossaboon | 260/645 |
|---|---|---|---|
| 3,816,551 | 6/1974 | Lee | 260/645 |
| 3,985,595 | 10/1976 | Benziger | 149/19.3 |

OTHER PUBLICATIONS

Benziger et al., "Pilot Plant Production of Triaminotrinitrobenezene (TATB)", LA-3632 (LASL).

Primary Examiner—Samuel W. Engle
Assistant Examiner—Donald P. Walsh
Attorney, Agent, or Firm—Dean E. Carlson; Edward C. Walterscheid

[57] ABSTRACT

Triaminotrinitrobenzene is readily formed by the nitration of 1,3,5-trichlorobenzene to 1,3,5-trichloro-2,4,6-trinitrobenzene followed by amination to triaminotrinitrobenzene. The purity of the triaminotrinitrobenzene is significantly improved if, during the amination step, sufficient water is present that the byproduct ammonium chloride formed during the amination is rendered at least semideliquescent.

3 Claims, No Drawings

METHOD FOR THE PRODUCTION OF HIGH-PURITY TRIAMINOTRINITROBENZENE

BACKGROUND OF THE INVENTION

The invention described herein relates to high explosives and, more particularly, to an improved process for preparing the high explosive sym-triaminotrinitrobenzene (TATB).

As taught in U.S. Pat. No. 3,985,595, filed Nov. 29, 1974 by the present inventor, the explosive compound TATB when combined with a halogenated plastic binder produces a plastic-bonded explosive composition which is heat resistant and highly insensitive. U.S. Pat. No. 3,985,595 also teaches that TATB is readily manufactured by the nitration of 1,3,5-trichlorobenzene (TCB) to 1,3,5-trichloro-2,4,6-trinitrobenzene (TCTNB) and the amination of the TCTNB to TATB.

The major impurity in TATB produced in accordance with the process taught in U.S. Pat. No. 3,985,595 is ammonium chloride, a byproduct of the amination of TCTNB to TATB. Smaller amounts of organic impurities, such as the partial amination products of tetrachlorodinitrobenzene, are also present. The relative concentration of these impurities in TATB is measured as percent chlorine, with 0.6% Cl being a typical value.

It has been found, however, that the presence of small amounts of ammonium chloride can produce serious compatibility problems in the use of TATB in certain types of ordnance. Accordingly, it is highly desirable that the process for forming TATB produce a TATB that is essentially free of ammonium chloride.

SUMMARY OF THE INVENTION

It has been found that, contrary to the teaching of the prior art, TCTNB is highly resistance to hydrolysis, and that the presence of a sufficient amount of water during the amination of TCTNB to TATB results in a product TATB that is essentially free of ammonium chloride. Accordingly, in the method for preparing TATB which comprises nitration of TCB to TCTNB followed by amination to TATB, the present invention resides in the improvement consisting of, in the amination step, adding sufficient water to the solvent for the TCTNB that the byproduct ammonium chloride formed during the amination is rendered at least semideliquescent. When this occurs the ammonium chloride no longer tends to occlude in the TATB and, as a result, the TATB crystals are essentially free of ammonium chloride.

In the process of the present invention, a preferred solvent for the TCTNB is toluene present in the ratio of about 10 parts toluene to one part TCTNB by weight. The presence of about 2.5% by weight of water in the toluene is effective to produce TATB that is essentially free of ammonium chloride.

EXAMPLE OF THE PRIOR ART PROCESS

According to the prior art the explosive compound TATB is readily manufactured according to the following steps:

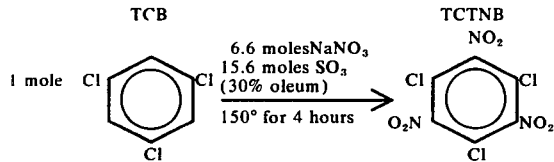

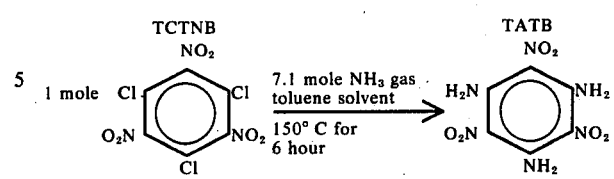

A pilot plant procedure for producing the TATB makes use of the following equipment:
1. A 10-gallon, glass-lined Pfaudler reactor capable of operation over a range of 20°–150° C and pressures to 100 psig; agitation is provided by an anchor-type blade at speeds of 20 to 200 rpm.
2. A glass-lined, concentric tube reflux condenser, integral with the Pfaudler reactor.
3. A 50-gallon, stainless steel reactor with agitator used in ice quenching of the nitration mixture.
4. Two 60-gallon, stainless steel receivers used in filtrate storage and recovery.
5. A stainless steel, 11 in. by 11 in. by 2 in. plate and frame filter press, closed delivery washing type.

Prior to the improvement of the present invention, the TATB was typically produced in the following manner. One hundred and twenty-six pounds of oleum are charged to the Pfaudler reactor, and 17 lb of sodium nitrate is then added at a slow rate with full agitation. The reaction is quite exothermic, and jacket cooling is used to keep the temperature at 60°–70° C. When the entire amount of NaNO₃ has been added and the exotherm peak has passed, the contents of the reactor are brought to a temperature of 100° C. The reactor is then charged with 5.5 lb of TCB, and steam is applied to the jacket to bring the temperature quickly to 145°–155° C. Only a small amount of exothermicity occurs in this step. The reactor contents are maintained at about 150° C for 4 hours. The small amounts of gas generated during the nitration are vented through the reflux condenser.

The contents of the Pfaudler reactor are then cooled to 40° C and discharged into the 50-gallon reactor which contains about 250 lb of crushed ice. Full agitation is used during this quench step, and the nitrous fumes are removed using a water-sealed vacuum pump. The TCTNB product precipitates in the form of heavy white crystals. The quenched reaction mixture is pumped through the plate and frame press which discharges into one of the 60-gallon holding tanks. Dynel cloth is readily used as the filtering medium. The cake is washed with several 20-gallon quantities of water, each followed with an air blow. This is continued until the wash water pH is 6–7. The cake is then dried in open trays in a forced-draft oven at 60° C for 16 hours.

In the amination step, 6 lb of TCTNB is dissolved in 60 lb of toluene, and the solution is clarified by filtration using Celite filter aid before transferring the mixture to the Pfaudler reactor. The reactor system is purged of any water by an atmospheric pressure distillation of the water-toluene azeotrope. Dryness of the system is indicated when the distillate changes from a cloudy, two-phase system to a clear liquid. When this occurs the reactor system is sealed, and heating is continued until the contents are at 145° C. Because the amination step is moderately exothermic, the jacket steam is turned off at this time. Ammonia gas is then added to the gas phase in the reactor through an opening on the top of the kettle. It is metered through a rotameter at a rate of about 0.8 lb/hr. When the $NH_3$ overpressure reaches about 5 psi, the reactor system is purged of residual air by venting through the reflux condenser. The system is then resealed, and the reaction is continued for a total of about three hours. Moderate agitation is used during this period. In the course of the reaction, which occurs at 150° C, the system pressure remains at 35–40 psig for most of the reaction period. This represents an $NH_3$ partial pressure of about 5–10 psi. As the reaction progresses, a small amount of jacket heating may be required to maintain the 150° C reaction temperature. The termination of the amination reaction is marked by a sharp rise in system pressure to about 60 psig.

When the pressure rise is noted, the $NH_2$ flow is stopped and the system is cooled to about 60° C. After the system is vented about 10 gallons of water are added with good agitation. The TATB product is recovered by filtration using the plate and frame press, equipped with cotton cloths backed with filter paper. The cake is washed three times with 20-gallon portions of water, interspersed with air blows. The cake is then steamed for about 10 minutes and air blown before removal from the press. It is then dried in open trays in a forced-draft oven at 100° C for 16 hours.

DESCRIPTION OF THE PREFERRED EMBODIMENTS

In the prior art process it was thought necessary to maintain the reaction system free of water during the amination step. This precaution was taken because of concern that the TCTNB intermediate would be subject to hydrolysis at the temperature required for amination. This was also the reason why the TCTNB was carefully dried before the amination step.

The improvement of the present invention is predicated on the discovery that not only does the system not have to be anhydrous during the amination step but that the presence of a certain amount of water is actually highly beneficial in that with water present during the amination step, the product TATB is essentially free of ammonium chloride. The reason for this is believed to be that the ammonium chloride crystals formed as a byproduct in amination were serving as nuclei for TATB crystal growth and as a result were being occluded as a major impurity in the TATB. In the presence of water the ammonium chloride deliquesces and assumes a semiliquid form not capable of serving as a nucleation center. The TATB crystals accordingly grow in a normal fashion free of the ammonium chloride impurity.

In a modification of the prior art pilot plant process herein described in accordance with the present invention, instead of purging the reaction system of water during the amination step, 2.5% by weight of water is added to the toluene solvent. Thus in the example given herein, wherein the ratio of 60 lb of toluene to 6 lb of TCTNB feed is used, the amount of water used is 1.5 lb. With this amount of water added, the product TATB contains only 0.20% Cl instead of the 0.6% Cl found in the product without the water addition. The amination yield is not diminished and the product has the proper elemental analysis. When water is present, the only change in process conditions is a moderate increase in system pressure. It will be apparent that when water is used there is no need to dry the feed TCTNB.

What I claim is:

1. In a method for preparing sym-triaminotrinitrobenzene which comprises nitration of 1,3,5-trichlorobenzene to 1,3,5-trichloro-2,4,6-trinitrobenzene followed by amination to sym-triaminotrinitrobenzene, the improvement which comprises, in the amination step, adding sufficient water to the solvent for the 1,3,5-trichloro-2,4,6-trinitrobenzene that the by-product ammonium chloride formed during the amination is rendered at least semideliquescent.

2. The method of claim 1 wherein said solvent is toluene present in the ratio of about 10 parts toluene to one part 1,3,5-trichloro-2,4,6-trinitrobenzene by weight.

3. The method of claim 2 wherein said water is about 2.5% by weight of said toluene.

* * * * *